United States Patent [19]

Waldron

[11] Patent Number: 5,092,869
[45] Date of Patent: Mar. 3, 1992

[54] OSCILLATING SURGICAL SAW GUIDE PINS AND INSTRUMENTATION SYSTEM

[75] Inventor: Stephen H. Waldron, Camarillo, Calif.

[73] Assignee: Biomet, Inc., Warsaw, Ind.

[21] Appl. No.: 662,742

[22] Filed: Mar. 1, 1991

[51] Int. Cl.$^5$ ...................... A61B 17/14; A61B 17/56
[52] U.S. Cl. ...................................... 606/82; 606/87; 606/88
[58] Field of Search ................... 606/82, 87–89, 606/86, 96, 172, 176–178; 623/20; 83/745

[56] References Cited

U.S. PATENT DOCUMENTS

| | | | |
|---|---|---|---|
| 2,708,465 | 5/1955 | Huebner et al. | 83/745 |
| 4,179,810 | 12/1979 | Kirsch . | |
| 4,340,060 | 7/1982 | Berke et al. . | |
| 4,409,973 | 10/1983 | Neufeld . | |
| 4,457,307 | 7/1984 | Stillwell | 83/745 X |
| 4,703,751 | 11/1987 | Pohl | 606/87 X |
| 4,708,133 | 11/1987 | Comparetto . | |
| 4,736,737 | 4/1988 | Fargie et al. . | |
| 4,759,350 | 7/1988 | Dunn et al. | 606/82 |
| 4,768,504 | 9/1988 | Ender . | |
| 4,791,919 | 12/1988 | Elloy et al. | 606/82 X |
| 4,892,093 | 1/1990 | Zarnowski et al. | 606/82 |
| 4,893,619 | 1/1990 | Dale et al. | 606/87 |
| 4,926,847 | 5/1990 | Luckman | 606/88 |
| 4,952,214 | 8/1990 | Comparetto | 606/87 |

FOREIGN PATENT DOCUMENTS

| | | | |
|---|---|---|---|
| 0125101 | 11/1984 | European Pat. Off. | 606/82 |
| 0243109 | 10/1987 | European Pat. Off. | 606/82 |

OTHER PUBLICATIONS

"AGC Total Knee System-Intramedullary with Distractor Surgical Technique," Biomet, Inc.

Primary Examiner—Randall L. Green
Assistant Examiner—David H. Willse
Attorney, Agent, or Firm—Ice Miller Donadio & Ryan

[57] ABSTRACT

An oscillating surgical saw and instrumentation system has an oscillating surgical saw and instrumentation for guiding the saw. The oscillating saw has a body or handle having guide pin holders disposed on opposite sides thereof and extending longitudinally therealong. Retractable guide pins are mounted in the guide pin holders. Resilient means are disposed in each guide pin holder which force the respective guide pin mounted therein longitudinally outward. The system further includes instrumentation for guiding the saw. The instrumentation comprises at least one cutting block. The cutting block is affixed to the bone being cut and has holes, which are preferably slots, for receiving the guide pins. These slots lie in planes which are parallel to planes in wich resected surfaces of the bone lie after they have been formed by cuts made to the bone.

When the saw is used to cut bone, the cutting block is secured to the bone and the guide pins inserted into the holes in the cutting block. The cutting block and guide pins cooperate to secure the saw, cutting block, and bone against movement in all planes except the plane in which the saw is cutting to reduce the transmission of vibration from the bone being cut through the saw. The associated guide pin holes guide the saw blade as it cuts bone. As the saw blade cuts progressively deeper into the bone, the guide pins are forced into their guide pin holders so as not to interfere with the advancement of the saw blade into the bone.

17 Claims, 5 Drawing Sheets

OSCILLATING SURGICAL SAW GUIDE PINS AND INSTRUMENTATION SYSTEM

BACKGROUND AND SUMMARY OF THE INVENTION

This invention relates to oscillating surgical saw and instrumentation systems, and more particularly to such systems used to shape bone, such as bone in a joint to conform it to a component of an artificial joint prosthesis.

Figure 1:
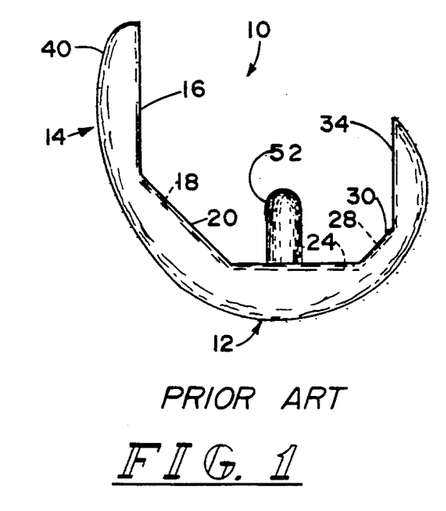
FIG. 1 shows a side view of a femoral component of an artificial knee.
Figure 2:
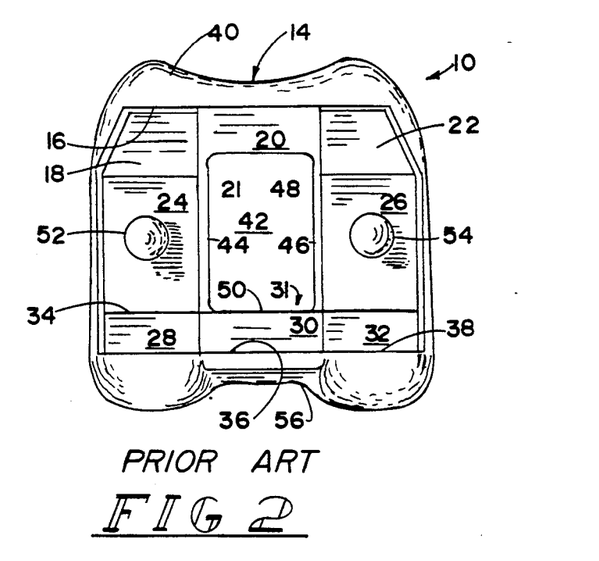
FIG. 2 shows a top plan view of the femoral component of FIG. 1.

This invention will be described in the context of artificial knees although it should be understood that the invention is not so limited. An artificial knee includes as one of its components a femoral component which replaces the condyles of the femur. An example of such a femoral component is illustrated in U.S. Pat. No. 4,892,547 to Brown for a Partially Stabilized Knee Prosthesis. As shown in FIGS. 1 and 2 of the '547 patent, reproduced here as FIGS. 1 and 2, the interior contours of a femoral component 10 has a plurality of surfaces which must match the surfaces of the femur after the femur has been prepared to receive femoral component 10. More specifically, femoral component 10 comprises a spaced-apart pair of downwardly convex bearing portions 12 which extend from the anterior side to the posterior side of component 10. The shapes of the outer surfaces of bearing portions 12 closely approximate the shapes of anatomical femoral condyles on the knee joint end of the femur. Femoral component 10 further comprises a generally vertically oriented patellar guide portion 14 which serves as a guide for the movements of a natural or prosthetic patella. The interior contours of femoral component 10 (which closely match the exterior contour of the end of the femur after the femur has been prepared to receive femoral component 10, i.e, the distal cut) are defined by generally vertical surface 16 on the posterior side of patellar guide portion 14, by posterior downwardly angled surfaces 18, 22 and 20 of bearing portions 12 and anterior intercondylar portion 21, respectively, by generally horizontal surfaces 24 and 26 of bearing portions 12, by posteriorly upwardly angled surfaces 28, 32 and 30 of bearing portions 12 and posterior intercondylar portion 31, respectively, and by vertically extending surfaces 34, 38 and 36 of bearing portions 12 and posterior intercondylar portion 31, respectively.

When femoral component 10 is implanted, the femur must be resected to fit the contours defined by internal surfaces 16–38 of femoral component 10. This is typically done by using an oscillating surgical saw and instrumentation system. The instrumentation guides the oscillating surgical saw as it is used to make the various resections in the femur so that the end of the resected femur matches closely the interior contours of femoral component 10. A technique and oscillating surgical saw and instrumentation system heretofore used in the knee replacement operation in which femoral component 10 is implanted is described in the brochure titled "AGC Total Knee System—Intramedullary with Distractor Surgical Technique" published by Biomet, Inc., ("AGC Total Knee System Brochure") which is attached hereto as Appendix A and incorporated herein by reference.

The oscillating surgical saw used to resect the femur usually has a blade which oscillates through a small arc on the order of four to six degrees at speeds of 15,000 to 20,000 cycles per minute. The excursion of the blade is necessarily short to permit the saw to cut in confined places. Moreover, the sharp teeth of the saw blade will cut rigid bone but if they contact soft tissue, the tissue will vibrate with the blade reducing the cutting of soft tissue.

Existing oscillating surgical saw and instrumentation systems used to resect the femur typically use cutting guides which have surfaces which transect the femur along planes which will match the planes in which the surfaces of the interior contours of femoral component 10 lie. In many cases, these surfaces are along slots which extend through the cutting block. However, the cutting block is typically held in place by hand and the saw guided along the cutting block by hand.

The problem with existing oscillating surgical saw and instrumentation systems is that vibration is transmitted from the blade of the oscillating surgical saw to the hands of the surgeon using the saw making it difficult to keep the saw aligned. More specifically, as the oscillating blade of the saw cuts into the bone, it will do so smoothly to a depth of about one centimeter. As the blade reaches a depth of about one centimeter, the blade begins to become trapped in the cut. When this happens, either the saw or the cutting block begins to oscillate. Consequently, the saw must be backed out of the cut to stop the vibration. To cut through the bone, the saw must be continuously inserted into and backed out of the cut. Otherwise, the blade will bind as described preventing the bone from being cut.

It is an objective of this invention to provide an oscillating surgical saw and instrumentation system that alleviates the vibration problem encountered by prior art systems.

It is also an objective of this invention to provide an oscillating surgical saw and instrumentation system where the saw, the instrumentation that guides the saw, and the bone are secured together against movement relative to one another in all planes except the plane in which the cut is being made.

It is also an objective of this invention to provide an oscillating surgical saw and instrumentation system where the instrumentation that guides the saw is affixed to the bone and the instrumentation, bone, and the saw are secured together against movement relative to one another in all planes except the plane in which the cut is being made and the instrumentation is configured to permit cuts through the bone in multiple planes without removal of the instrumentation from the bone.

An oscillating surgical saw and instrumentation system according to this invention has an oscillating surgical saw and instrumentation for guiding the saw. The oscillating saw has a body or handle having guide pin holders disposed on opposite sides thereof and extending longitudinally therealong. Retractable guide pins are mounted in the guide pin holders. Resilient means are disposed in each guide pin holder which force the respective guide pin mounted therein longitudinally outward. The system further includes instrumentation for guiding the saw. The instrumentation comprises at least one cutting block. The cutting block is affixed to the bone being cut and has holes for receiving the guide pins and can have slots through which the saw blade passes. The guide pin holes are preferably slots and lie in planes which are parallel to planes in which resected surfaces of the bone lie after they have been formed by cuts made to the bone.

When the saw is used to cut bone, the cutting block is secured to the bone and the guide pins inserted into the holes in the cutting block. The cutting block and guide pins cooperate to secure the saw against movement in all planes except the plane in which the saw is cutting to reduce the transmission of vibration from the bone being cut through the saw. The guide pin holes guide the saw blade as it cuts bone. As the saw blade cuts progressively deeper into the bone, the guide pins are forced into their guide pin holders so as not to interfere with the advancement of the saw blade into the bone.

Other objects, advantages and novel features of the present invention will become apparent from the following detailed description of the invention when considered in conjunction with the accompanying drawings.

DETAILED DESCRIPTION OF THE DRAWINGS

Figure 5:
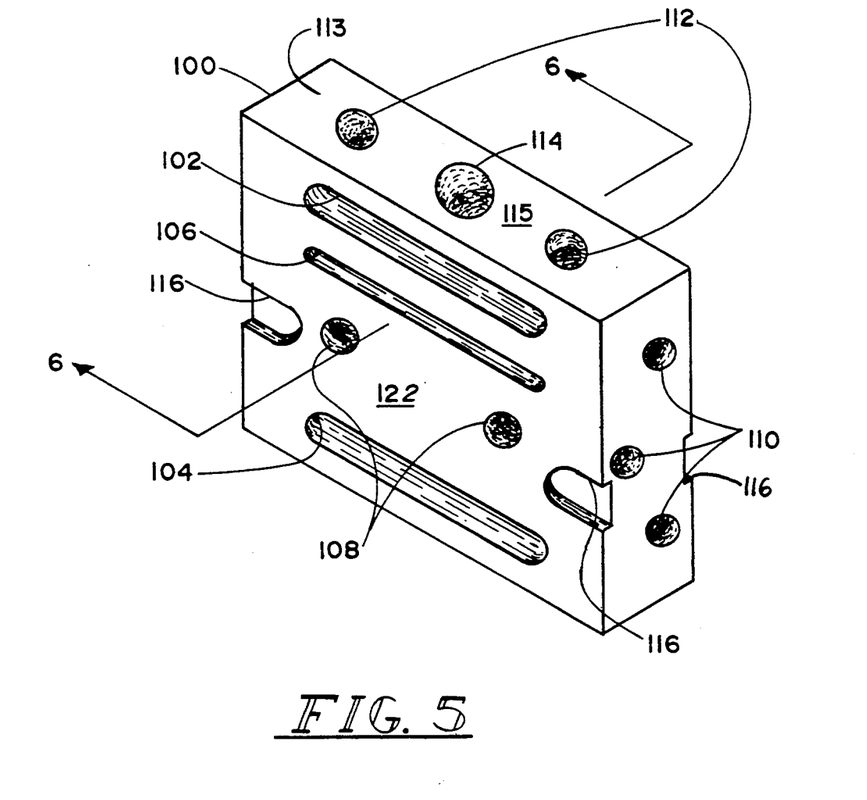
FIG. 5 shows a perspective view of an anterior/posterior cutting block according to this invention from the side which faces away from the bone when the block is in use.
Figure 6:
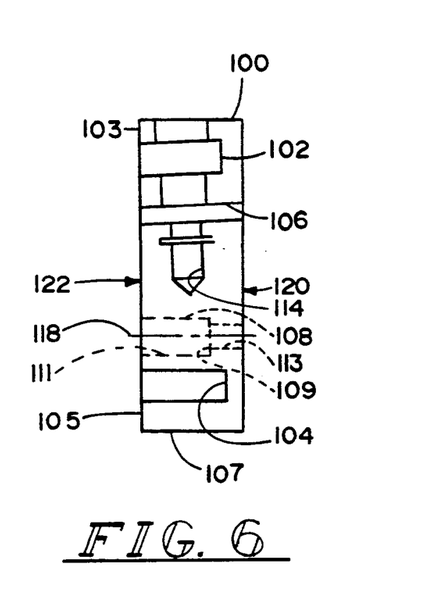
FIG. 6 is a sectional view taken along the line 6—6 of FIG. 5.
Figures 7, 8:
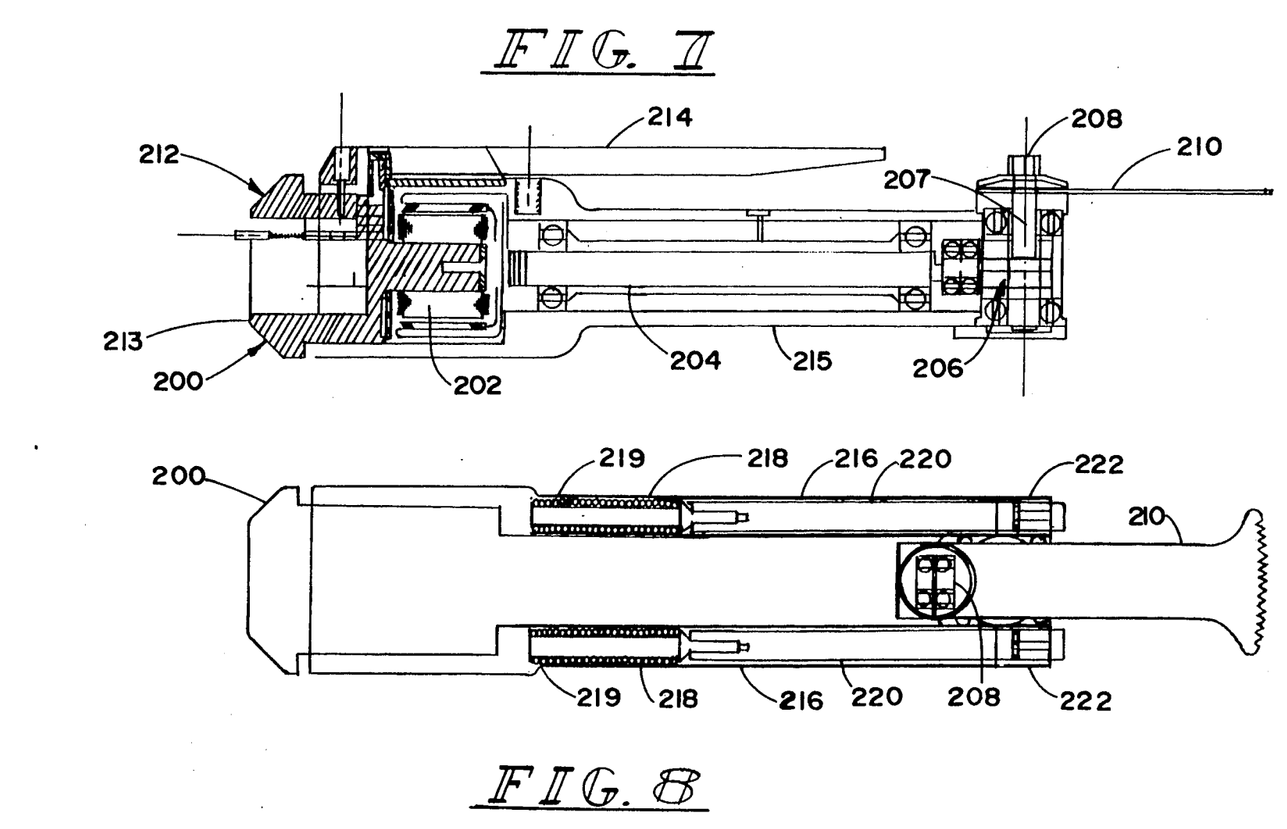
FIG. 7 is a side perspective view of an oscillating surgical saw according to this invention.
FIG. 8 is a side perspective view of the oscillating surgical bone saw of FIG. 7 rotated ninety degrees.

Referring to FIGS. 3-8, an oscillating surgical saw and instrumentation system according to this invention comprises a chamfer cutting block 60 (FIGS. 3 and 4), an anterior/posterior cutting block 100 (FIGS. 5 and 6), and an oscillating surgical saw 200 (FIGS. 7 and 8). Chamfer cutting block 60 and anterior/posterior cutting block 100 are for use in resecting the end of a femur to shape it to receive the femoral component of an artificial knee such as femoral component 10 shown in FIGS. 1 and 2. Alternatively, combined cutting block 300 (FIG. 9) can be used in place of chamfer cutting block 60 and anterior/posterior cutting block 100. It should be understood, however, that this invention is not limited to shaping femurs for artificial knee implants but is useful for any operation where bone must be shaped with an oscillating surgical saw. The cutting blocks used with oscillating surgical saw 200 are configured so that the appropriate resections of the bone can be made using oscillating surgical saw 200.

Figure 10:
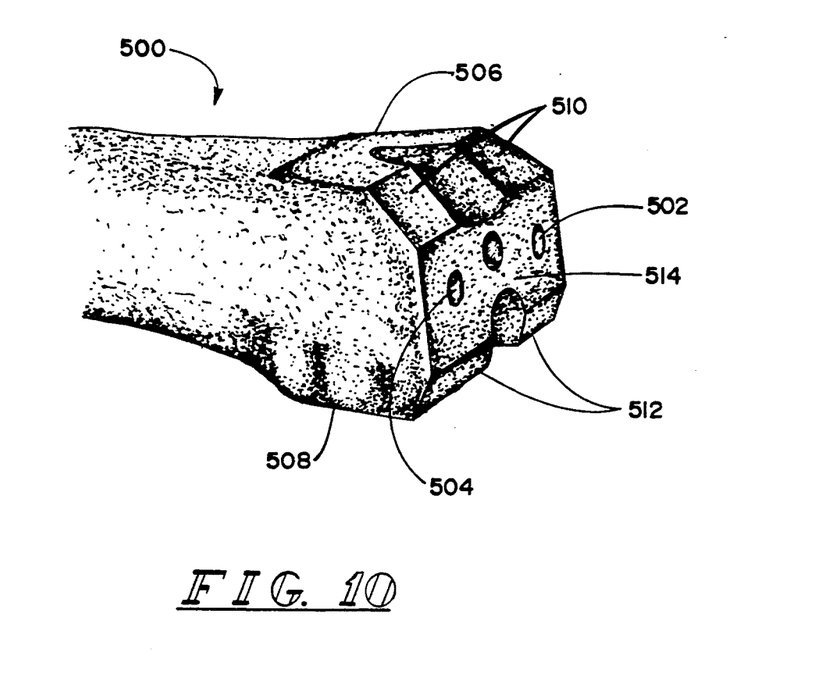
FIG. 10 is a perspective view of the end of a femur which has been resected to receive the femoral component of FIGS. 1 and 2.

Again in the context of an artificial knee and with regard to femoral component 10 of FIGS. 1 and 2, the end of a femur 500 (FIG. 10) is cut in five planes at angles to each other to match it to the interior contours of femoral component 10. The ends of the condyles of the femur are first trimmed in a plane perpendicular to the mechanical axis of the femur. This trim cut, known as the primary distal femoral trim, is to assist in positioning the femoral component 10 in the saggital plane while making a minimal resection. This cut is illustratively made using known techniques and instrumentation. (See, AGC Total Knee System Brochure at Tabs 2-3.) Next, the femoral component is sized and oriented, again using known techniques, and two holes 502, 504 (FIG. 10) drilled in the distal femur. (See, AGC Total Knee System Brochure at Tabs 4 or 4a.) An anterior cut and a posterior cut resulting in anterior resected surface 506 and posterior resected surface 508 (FIG. 10) are then made to the end of the femur 500. (See, AGC Total Knee System Brochure at Tab 5 which describes the known technique and instrumentation.) The anterior resected surface 506 is ninety-three degrees to the primary distal femoral trim 35 cut, i.e., three degrees to the mechanical axis of the femur, and the posterior resected surface 508 is perpendicular to or 90 degrees to the distal femoral trim plane cut, i.e., parallel to the mechanical axis of the femur. With respect to shaping the femur 500, the final distal femoral cut is now made using conventional techniques and instrumentation resulting in final distal femoral resected surface 514 (FIG. 10). (See, AGC Total Knee System Brochure at Tabs 8-9). An anterior chamfer cut and a posterior chamfer cut are now made resulting in anterior chamfer resected surface 510 and posterior chamfer resected surface 512 (FIG. 10). (See, AGC Total Knee System Brochure at Tab 10 which describes the known technique and instrumentation.) With regard to femoral component 10 shown in FIGS. 1 and 2, the interior and the posterior chamfer resected surfaces 510, 512 will be at 45 degrees to the final distal resected surface 514. The remainder of the knee replacement operation proceeds as described in the AGC Total Knee System Brochure.

The embodiment of the invention described herein relates to an improved oscillating surgical saw and instrumentation system for making the anterior and posterior cuts and the anterior and posterior chamfer cuts. Chamfer cutting block 60 and anterior/posterior cutting block 100 are used with oscillating surgical saw 200 in accordance with this invention to make the anterior and posterior cuts and the anterior and posterior chamfer cuts.

Figure 3:
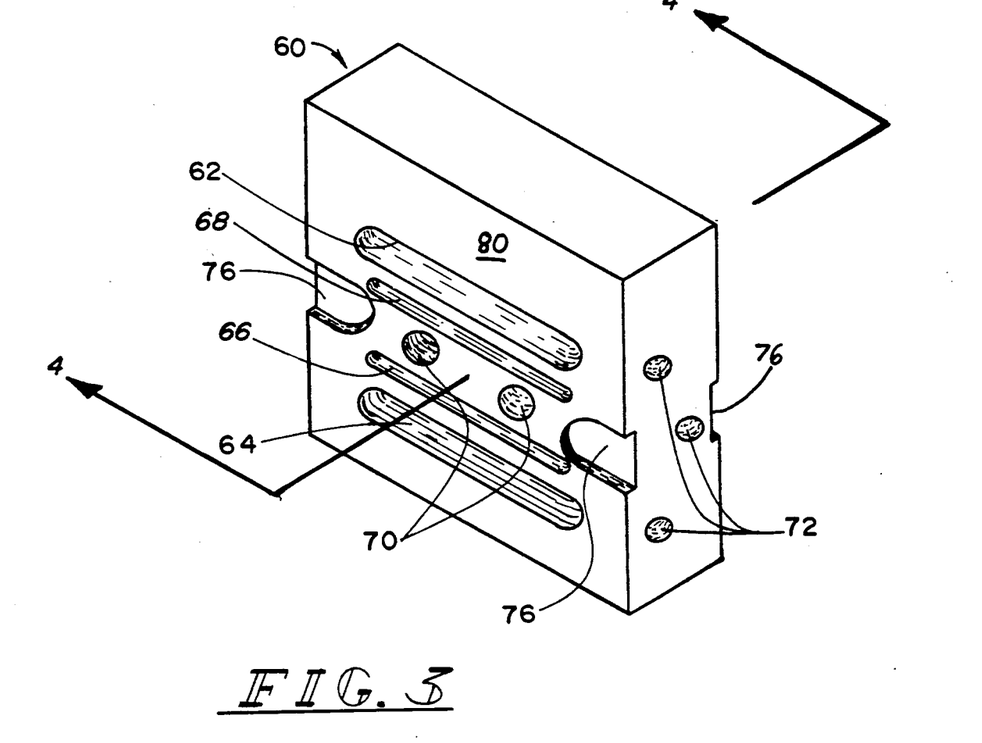
FIG. 3 shows a perspective view of a chamfer cutting block according to this invention from the side which faces away from the bone when the block is in use.
Figure 4:
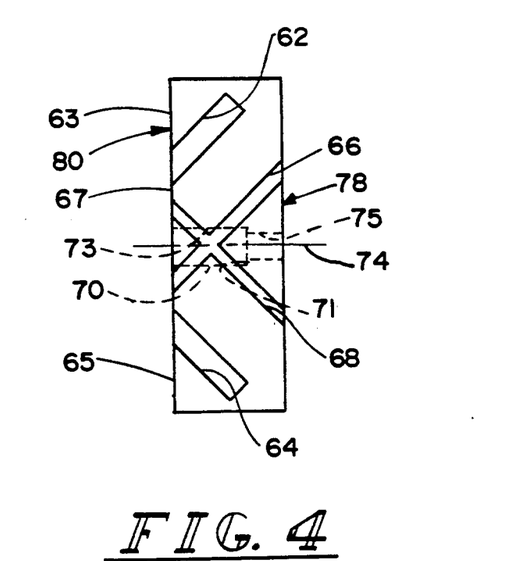
FIG. 4 is a sectional view taken along the line 4—4 of FIG. 3.

Referring to FIGS. 3 and 4, chamfer cutting block 60 comprises a generally rectangular block made from an appropriately rigid material such as steel. Chamfer cutting block 60 has a transverse axis 74 extending transversely therethrough. Chamfer cutting block 60 further includes a first guide pin slot 62 extending partially through an upper portion 63 thereof and a second guide pin slot 64 extending partially through a lower portion 65 thereof. Chamfer cutting block 60 also includes a first saw blade slot 66 and a second saw blade slot 68 both of which extend through a generally central portion 67 of chamfer cutting block 60 entirely through chamfer cutting block 60. Chamfer cutting block 60 has a femoral contacting surface 78 which abuts the distal resected surface 514 of femur 500 (FIG. 10) when chamfer cutting block 60 is in use and a femoral non-contacting surface 80 on the side opposite femoral contacting surface 68.

The first guide pin slot 62 and first saw blade slot 66 extend parallel to each other and, as viewed in the drawings, upwardly through chamfer block from femoral non-contacting surface 80 toward femoral contacting surface 68 at a 45 degree angle to transverse axis 64. First guide pin slot 62 is spaced from first saw blade slot 66 a distance which is equal to the offset between the plane in which guide pins 220 of oscillating surgical saw 200 lie and the plane in which saw blade 210 of oscillating surgical saw 200 lies (FIGS. 7 and 8).

Second guide pin slot 64 and second saw blade slot 68 extend parallel to each other and, as viewed in the drawings, downwardly through chamfer cutting block 60 from femoral non-contacting surface 80 toward femoral contacting surface 68 also at a forty-five degree angle to transverse axis 74. First and second guide pin slots 62, 64 are thus at ninety degree angles to each other as are first and second saw blade slots 66, 68. Second guide pin slot 64 is similarly spaced a distance from second saw blade slot 68 which is equal to the distance that guide pins 220 of oscillating surgical saw 200 are spaced from the saw blade 210 of oscillating surgical saw 200.

Chamfer cutting block 60 preferably includes two peg holes 70 extending transversely therethrough. Peg holes 70 are "stepped" in that a distal portion 73 which extends from the femoral non-contacting surface 80 partially through chamfer cutting block 60 has a larger diameter than a proximal portion 75 which extends the rest of the way through chamfer cutting block 60 and opens at femoral contacting surface 78. The junction of distal portion 73 and proximal portion 75 forms an annular shoulder 71. Peg holes 70 cooperate with pegs 600 (FIG. 11) to locate and secure chamfer cutting block 60 to distal resected femoral surface 514 of femur 500 when chamfer cutting block 60 is in use as will be discussed later.

Chamfer cutting block 60 can also include threaded holes 72 formed in opposite ends thereof so that a bone clamp (not shown) can be affixed to chamfer cutting block 60 as will be discussed later. Chamfer cutting block 60 also includes retraction recesses 76 formed in femoral contacting surface 78 and femoral non-contacting surface 80 on opposite sides of chamfer cutting block 60. Retraction recesses 76 facilitate the removal of chamfer cutting block 60 from the resected surface of a femur as will be discussed later.

Referring to FIGS. 5 and 6, anterior/posterior cutting block 100 comprises a generally rectangular block made from an appropriately rigid material such as steel. Anterior/posterior cutting block 100 has a transverse axis 118 extending transversely therethrough. Anterior/posterior cutting block 100 has a first guide pin slot 102 extending partially through an upper portion 103 thereof and a second guide pin slot 104 extending transversely partially through a lower portion 105 thereof. Anterior/posterior cutting block 100 also includes a saw blade slot 106 extending transversely and entirely through the upper portion 103 thereof parallel to and in spaced relation to first guide pin slot 102. Anterior/posterior cutting block 100 has a femoral contacting surface 120 and a femoral non-contacting surface 122 on the side opposite from femoral contacting surface 120.

First guide pin slot 102 is spaced from saw blade slot 106 a distance equal to the distance between guide pins 220 of oscillating surgical saw 200 and saw blade 210 of oscillating surgical saw 200. The first guide pin slot 102 and saw blade slot 106 extends parallel to each other and, as viewed in the drawings, generally upwardly through anterior/posterior cutting block 100 from femoral non-contacting surface 122 toward femoral contacting surface 120 at an angle of three degrees to transverse axis 118. Second guide pin slot 104 extends partially through anterior/posterior cutting block 100 parallel to transverse axis 118. Second guide pin slot 104 is spaced from a lower edge 107 of anterior/posterior cutting block 100 a distance no more than the distance between guide pins 220 of oscillating surgical saw 200 and saw blade 210. Thus, when anterior/posterior cutting block 100 is being used and the guide pins 220 of oscillating surgical saw 200 are received in guide pin slot 104, as described later, the saw blade 210 will pass below the lower edge 107 of anterior/posterior cutting block 100 so that there is no need for a saw blade slot associated with guide pin slot 104 to be formed in anterior/posterior cutting block 100.

Anterior/posterior cutting block 100 preferably includes two peg holes 108 extending transversely therethrough. Peg holes 108 are identical to peg holes 20 formed in chamfer cutting block 10. The junction of the larger diameter distal portion 111 of peg hole 108 and the smaller diameter proximal portion 113 forms an annular shoulder 109. Peg holes 108 cooperate with pegs 600 (FIG. 11) to secure anterior/posterior cutting block 100 to femur 500 after the primary distal femoral trim cut has been made but before the final distal femoral cut has been made as will be discussed later.

Anterior/posterior cutting block 100 also includes threaded holes 110 formed in opposite ends thereof to permit a bone clamp (not shown) to be affixed to anterior/posterior cutting block 100 as will be discussed later. Anterior/posterior cutting block 100 also includes alignment guide holes 112 extending downwardly from a top surface 115 of anterior/posterior cutting block 100 on generally opposite sides thereof and a stylus hole 114 which extends downwardly from top surface 115 of anterior/posterior cutting block 100 generally in the center thereof. Anterior/posterior cutting block 100 also includes retraction recesses 116 formed in femoral contacting surface 120 and femoral non-contacting surface 122 on opposite sides of anterior/posterior cutting block 1??. Retraction recesses 116 facilitate the removal of anterior/posterior cutting block 100 from femur 500 after it has been affixed in place.

Referring to FIGS. 7 and 8, oscillating surgical saw 200 is shown. It should be understood that oscillating surgical saw 200 is, with the exception of the modifications discussed herein, similar to commercially available oscillating surgical saws such as a 5048-02 saw manufactured by Hall Surgical. Oscillating surgical saw 200 has a handle or body 212. Body 212 has an enlarged distal portion 213 and an elongated proximal portion 215 which extends from enlarged distal portion 213. A drive motor 202 is disposed in the distal portion 213 of handle 212. A drive shaft 204 is disposed within handle 212 and has one end coupled to drive motor 202 and extends through the proximal portion 215 of handle 212 and is coupled at its other end to an oscillating mechanism 206. Oscillating mechanism 206 is mounted in handle 212 at the end of proximal portion 215. A coupling mechanism 207 extends transversely out through the proximal portion 215 of handle 212 from oscillating mechanism 206 and couples oscillating mechanism 206 to a saw blade holder 208. Saw blade holder 208 holds a saw blade 210. A speed control lever 214 is mounted to elongated distal portion 213 of handle 212 and is coupled to drive motor 202 to control the speed of drive motor 202. Except that body 212 is elongated, the elements of surgical saw 200 described to this point correspond to the elements of commercially available oscillating surgical saws.

Oscillating surgical saw 200 further includes a pair of longitudinally extending guide pin holders 216 on opposite sides of proximal portion 215 of handle 212. Guide pin holders 216 lie in a plane which is parallel to the plane in which saw blade 210 cuts. Compression springs 218 are disposed in distal ends 219 of guide pin holders 216. Guide pins 220 are received in guide pin holders 216. Guide pin holders 216, compression springs 218 and guide pins 220 are features of this invention and are elements which commercially available oscillating surgical saws do not have. Guide pin holders 216 also include locking mechanisms 222 in proximal ends thereof so that the guide pins can be locked in a retracted position in the guide pin holders 216. Locking mechanisms 222 can be any conventional type of locking mechanism which will lock a spring biased member in place when it has been pushed against a spring.

Figure 11:
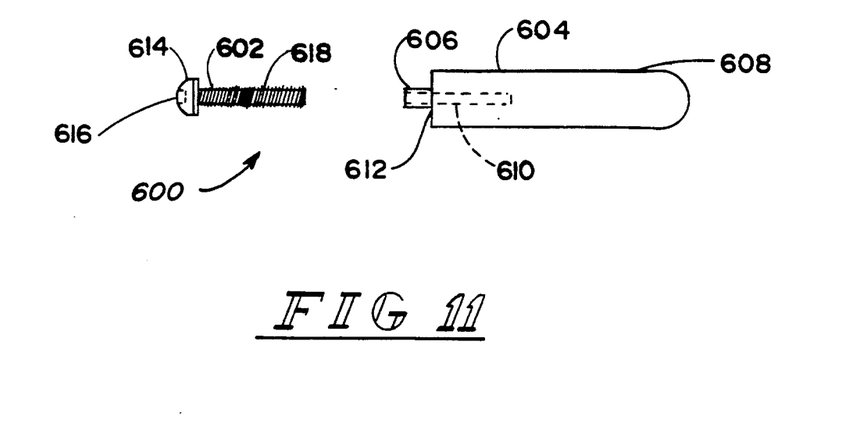
FIG. 11 is a side perspective view of a peg used to locate and secure the cutting blocks of FIGS. 3-6 and 9 to the end of a femur.

Referring to FIG. 11, a peg 600 for locating and securing chamfer cutting block 60 or anterior/posterior cutting block 100 to femur 500 is shown. Peg 600 is illustratively two-pieces comprising a screw 602 and a shaft 604. Screw 602 has a head 614 having a hex-slot 616 formed therein for receiving a hex-driver (not shown) and a threaded shank 618. Head 614 has a diameter slightly smaller than the diameter of the distal portions 73, 111, of peg holes 70, 108, in chamfer cutting block and anterior/posterior cutting block 60, 100, respectively, and larger than the diameter of proximal portions 75, 113 of peg holes 70, 108. Threaded shank of 618 screw 602 has a diameter smaller than the diameter of proximal portions 75, 113 of peg holes 70, 108, and is threadably received in threaded distal portion 606 of shaft 604 as will be discussed later.

Shaft 604 has a distal portion 606 and an elongated proximal portion 608. Distal portion 606 and elongated proximal portion 608 of shaft 604 included threaded hole 610 which extends through distal portion 606 into proximal portion 608. The diameter of distal portion 606 is slightly smaller than the diameter of proximal portions 75, 113, of peg holes 70, 108, of chamfer cutting block 60 and anterior/posterior cutting block 100, and is also smaller than the diameter of elongated proximal portion 608 of shaft 604 which is larger than the diameter of proximal portions 75, 113 of peg holes 70, 108. The junction of distal portion 606 and proximal portion 608 of shaft 604 forms annular shoulder 612.

Typically, two pegs 600 are used to secure and located chafer cutting block 60 and anterior/posterior cutting block 100 on a femur such as femur 500 (FIG. 10). Pegs 600 are typically pre-assembled to cutting blocks 60, 100 by inserting distal portions 606 of shaft 604 of pegs 600 into the proximal portions 75, 113, of peg holes 70, 108, as the case may be. Screws 602 are then inserted in distal portions 73, 111, of peg holes 70, 108, and tightened into the distal portions 606 of shafts 604. Heads 614 of screws 502 will butt against annular shoulders 71, 109, of peg holes 70, 108, and cooperate with shafts 604 to secure pegs 600 to chamfer cutting block 60 and anterior/posterior cutting block 100.

The use of the guided oscillating surgical saw and instrumentation of this invention is now described. After the distal femoral trim cut has been made end holes 502, 504 drilled in the distal end of femur 500, the anterior and posterior cuts are made using anterior/posterior cutting block 100. Although the following description refers to femur 500, it should be understood that the final distal femoral cut has not yet been made so final distal femoral resected surface 514 has not yet been formed. Holes 502, 504 are spaced apart the same distance as peg holes 108 in anterior/posterior cutting block 100. Anterior/posterior cutting block 100 is now positioned on the distal end of femur 500 with femoral contacting surface 120 abutting the distal end of femur 500 and shafts 604 of pegs 600, which will typically have been pre-assembled to anterior/posterior cutting block 100 as discussed, inserted into holes 502, 504 in femur 500. Pegs 600 properly locate anterior/posterior cutting block 100 on the distal end of femur 500 and also secure it in place.

After anterior/posterior cutting block 100 has been secured to femur 500, the anterior cut and the posterior cut are made using oscillating surgical saw 200. Guide pins 220 are unlocked in guide pin holders 216 and are forced outwardly alongside the saw blade 210 in spaced relation thereto by compression springs 218. Guide pins 220 are first inserted in first guide pin slot 102 and saw blade 210 is inserted into saw blade slot 106. Oscillating surgical saw 200 is then advanced until saw blade 210 contacts the femur 500. Oscillating surgical saw 200 cuts the anterior of the femur 500 to make the anterior cut and form anterior resected surface 506. The guide pin slot 102 and saw blade slot 106 are preferably elongated to permit the saw blade 210 to be moved transversely in anterior/posterior cutting block 100 to fully make the anterior cut. However, guide pin slots 102 could also comprise a pair of cylindrical holes in which case oscillating surgical saw 200 could only move in and out of anterior/posterior cutting block 100 but not transversely. Oscillating surgical saw 200 is then retracted and guide pins 220 next inserted in second guide pin slot 104. As mentioned, guide pin slot 104 is spaced from the lower edge 107 of anterior/posterior cutting block 100, as oriented in the drawings, so that saw blade 210 passes beneath the lower edge 107. Oscillating surgical saw 200 is advanced to bring saw blade 210 into contact with the posterior of femur 100 and the posterior cut made to form posterior resected femoral surface 508. Guide pin slot 104 is also preferably elongated to permit the saw blade to be moved transversely therein but could also comprise a pair of cylindrical holes. Thereafter, as discussed above, the final distal femoral cut is made to form final distal femoral resected surface 514.

Chamfer cutting block 60 is now used to make the anterior and posterior chamfer cuts to form anterior and posterior resected chamfer surfaces 510, 512. Chamfer cutting block 60 is positioned on final distal femoral resected surface 514 of femur 500 and the shafts 604 of pegs 600 inserted into holes 502, 504 in femur 500 to position chamfer cutting block 60 on final distal femoral resected surface 514 and secure it to femur 500.

After chamfer cutting block 60 has been secured to femur 500, oscillating surgical saw 200 is used to make the anterior chamfer cut and the posterior chamfer cut. This forms anterior and posterior resected chamfer surfaces 510, 512 which are at angles of forty-five degrees to the mechanical axis of the femur.

Guide pins 220 of oscillating surgical saw 200, assuming that they are unlocked and extended, are inserted into first guide pin slot 62 and saw blade 210 inserted into first saw blade slot 66. Surgical saw 200 is then advanced until saw blade 210 contacts the femur 500. Oscillating surgical saw 200 cuts the anterior of the femur to make the anterior chamfer cut and form anterior resected chamfer surface 510. First guide pin slot 62 and first saw blade slot 66 are preferably elongated to permit the guide pins 220 and the saw blade 210 to be moved transversely therein. This permits the chamfer cut to be made to both condyles of femur 500 without relocating oscillating surgical saw 200. Oscillating surgical saw is then retracted and guide pins 220 inserted in second guide pin slot 64 and saw blade 210 inserted in second saw blade slot 68 to make the posterior chamfer cut to form posterior resected chamfer surface 512. Second guide pin slot 64 and second saw blade slot 68 are also preferably elongated to permit the guide pins 220 and saw blade 210 be moved transversely therein. First and second guide pin slots 62, 64 could also each comprise a pair of cylindrical holes.

In accordance with this invention, guide pins 220 cooperate with chamfer cutting block 60 or anterior/posterior cutting block 100 to secure oscillating surgical saw 200 against movement in all planes except the plane in which saw blade 210 is cutting. Consequently, as the saw blade 210 cuts deeper and deeper into femur 500, any vibration caused by saw blade 210 beginning to clog up will be damped by the cooperation of guide pins 220 in a guide pin slot of chamfer cutting block 60 or anterior/posterior cutting block 100. Moreover, the elongation of handle 212 of oscillating surgical saw 200 will help damp any residual vibration thus minimizing the amount of vibration transmitted from saw blade 210 to the hands of the surgeon. Also, as oscillating surgical saw 200 is advanced to cut the bone, guide pins 220 are forced against compression springs 218 into guide pin holders 216 so as not to prevent advancement of oscillating surgical saw 200.

Chamfer cutting block 60 and anterior/posterior cutting block 100 are removed from femur 500 by use of a forceps-like removal tool (not shown). This tool has opposed fingers which are inserted in extraction recesses 76 of chamfer cutting block 10 or extraction recesses 116 of anterior/posterior cutting block 100. Chamfer cutting block 60 or anterior/posterior cutting block 100 is then pulled from femur 500 pulling pegs 600 out of holes 502, 504.

In addition to or alternative to pegs 600, two bone clamps 700 (FIG. 12) can be used to secure chamfer cutting block 60 or anterior/posterior cutting block 100 to femur 500. Bone clamp 700 comprises a triangular shaped flange 702 having securing holes 704, 706 extending therethrough at two corners thereof and drill holes 708, illustratively three, extending therethrough at the third corner thereof. Bone clamp 700 also includes bolts 710.

Figure 12:
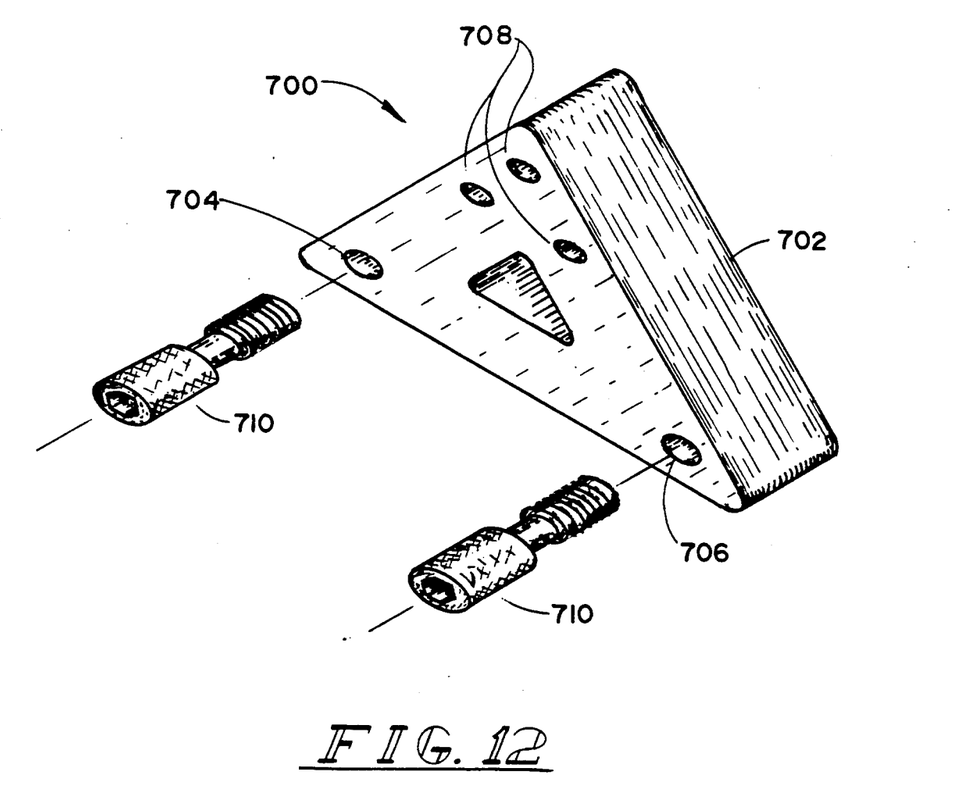
FIG. 12 is a perspective view of a bone clamp.

In use, a bone clamp 700 is secured to each side of a chamfer cutting block 60 or an anterior/posterior cutting block 100 by bolts 710 which extend through holes 704, 706 in triangular flange 702 and are tightened in threaded holes 72 of chamfer cutting block 60 or threaded holes 110 of anterior/posterior cutting block 100. The end of triangular flange 702 with drill holes 708 extends along femur 500 when the cutting block to which it is secured is positioned on femur 500. Drill bits are inserted in each drill hole 708, in turn, and holes drilled in femur 500. The drill bits are left in place in femur 500 and extend out through drill holes 708 in triangular flange 702 which holds the cutting block to which the clamp 700 is secured to femur 500.

Alignment holes 112 in anterior/posterior cutting block 100 are for use in affixing an alignment tower (not shown) to anterior/posterior cutting block 100. The alignment tower is similar in concept to the extramedullary alignment tower shown schematically at Tab 3 of the AGC Total Knee System Brochure in that it is used to check the valgus angle. The alignment tower is used to check the valgus angle after the anterior/posterior cutting block 100 is positioned on the distal end of femur 500 and secured thereto.

Stylus hole 114 permits a stylus (not shown) to be used to locate anterior/posterior cutting block 100 on the distal end of femur 500 in revision cases, i.e., where there are no posterior condyles. This could occur due to severe deterioration of the condyles of the femur or where an artificial knee has been previously implanted and is being replaced. The stylus is similar in concept to the one shown schematically at Tab 1a of the AGC Total Knee System Brochure for use with the tibia. The stylus is inserted in stylus hole 114 in anterior/posterior cutting block 100 and moved down until it touches the anterior cortex of the femur. This shows where the anterior flange of femoral component 10 (FIGS. 1 and 2) will contact the femur and from this location holes 502, 504 can be located and drilled.

Figure 9:
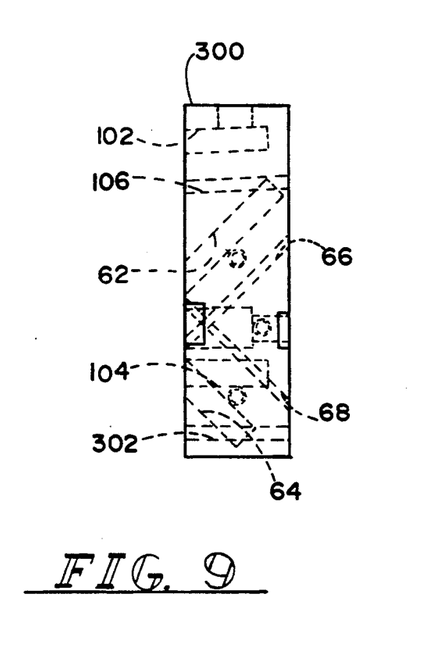
FIG. 9 is a side view of a combined chamfer and anterior/posterior cutting block according to this invention.

FIG. 9 shows a combined chamfer cutting and anterior/posterior cutting block 300. Combined cutting block 300 includes the first and second guide pin slots 62 and 64 and the first and second saw blade slots 66 and 68 for use in making the chamfer cuts. Combined cutting block 300 also includes the first and second guide pin slots 102, 104 and the saw blade slot 106 for use in making the anterior and posterior cuts. Moreover, combined cutting block 300 also includes saw blade slot 302 associated with guide pin slot 104 for use in making the posterior cut. Saw blade slot 302 is required because to accommodate guide pin slot 14 for use in making one of the chamfer cuts the height of combined cutting block 300 is such that the saw blade 210 cannot pass beneath a bottom edge of combined cutting block 300.

From the preceding description of the preferred embodiment it is evident that the objects of the invention are attained. Although the invention has been described and illustrated in detail, it is to be clearly understood that the same is intended by way of illustration and example only and is not to be taken by way of limitation. The spirit and scope of the invention are to be limited only by the terms of the appended claims.

What is claimed is:

1. An oscillating surgical saw and instrumentation system for use in cutting a bone to shape the bone comprising:
 an oscillating surgical saw having a body, the body having means for holding a saw blade and means for oscillating the saw blade, the body further including first and second guide pins disposed on opposite sides of the body and extending longitudinally therefrom in a plane parallel to a cutting plane in which the saw blade cuts;
 the instrumentation comprising at least one cutting block having at least one opening therein for receiving the first and second guide pins;
 means for securing the cutting block on the bone being cut in a predetermined position;

wherein the guide pins of the saw body received in the opening of the cutting block when the saw is cutting bone cooperate with the cutting block to secure the saw against movement in all planes except the cutting plane to reduce the transmission of vibration from the saw blade through the saw.

2. The apparatus of claim 1 wherein the body of the saw includes means for retractably holding the guide pins and resilient means disposed in the holding means for urging the guide pins longitudinally outward from the holding means.

3. The apparatus of claim 1 wherein the opening in the cutting block comprises a slot.

4. The apparatus of claim 3 wherein the cutting block further includes a saw blade slot extending therethrough through which the saw blade passes, the slot lying in a plane parallel to a plane in which said first recited slot lies.

5. The apparatus of claim 3 wherein the cutting block includes a plurality of guide pin slots extending at least partially therethrough, where when the cutting block is secured to the bone each slot lies in a plane which is parallel to a plane in which the bone is to be cut.

6. The apparatus of claim 1 wherein the means for securing the cutting block on the bone being cut comprises the cutting block having a plurality of stepped holes extending transversely therethrough and pegs which are received in the stepped holes of the cutting block and have distal ends extending therefrom where when the cutting block is secured to the bone the pegs extend into holes formed in the bone to which the cutting block is to be secured to secure the cutting block to the bone.

7. The apparatus of claim 1 wherein the apparatus is for use in shaping the end of a femur to receive a femoral component of an artificial knee and said at least one cutting block of the instrumentation of the apparatus comprises a plurality of cutting blocks including a chamfer cutting block for use in making anterior and posterior chamfer cuts to the femur to form anterior and posterior resected chamfer surfaces on the femur and an anterior/posterior cutting block for use in making anterior and posterior cuts to the femur to form anterior and posterior resected surfaces on the femur;

the chamfer cutting block having first and second guide pin slots extending transversely and at least partially therethrough where when the chamfer cutting block is affixed to the femur the first guide pin slot lies in a plane parallel to a plane in which the anterior resected chamfer surface of the femur lies after it has been formed and the second guide pin slot lies in a plane parallel to a plane in which the posterior resected chamfer surface of the femur lies after it has been formed;

the anterior/posterior cutting block having first and second guide pin slots extending transversely and at least partially therethrough where when the anterior/posterior cutting block is affixed t the femur the first guide pin slot lies in a plane parallel to a plane in which the anterior resected surface of the femur lies after it has been formed and the second guide pin slot lies in a plane parallel to a plane in which the posterior resected surface of femur lies after it has been formed;

the first and second guide pin slots of the chamfer cutting block and the first and second guide pin slots of the anterior/posterior cutting block receiving the guide pins of the oscillating surgical saw as it is used to make the anterior and posterior chamfer cuts and the anterior and posterior cuts, respectively, to secure the saw against movement inn all planes except the plane in which the respective cut is being made.

8. The apparatus of claim 7 wherein the chamfer cutting block has first and second saw blade slots extending transversely therethrough associated with the first and second guide pin slots, respectively, where when the chamfer cutting block is affixed to the femur the first saw blade slot lies in the plane in which the anterior resected chamfer surface of the femur will lie after it has been formed and the second saw blade slot lies in the plane in which the posterior resected chamfer surface of the femur will lie when it has been formed, the anterior/posterior cutting block having a saw blade slot extending transversely therethrough associated with the first guide pin slot where when the anterior/posterior cutting block is affixed to the femur the saw blade slot lies in the plane in which the anterior resected surface of the femur will lie when it has been formed, the anterior/posterior cutting block having an edge associated with the second guide pin slot which is spaced a distance from the second guide pin slot such as to permit the saw blade of the oscillating surgical saw to pass by the edge when the guide pins of the oscillating surgical saw are received in the second guide pin slot of the anterior/posterior cutting block.

9. The apparatus of claim 1 wherein the saw body comprises an elongated body.

10. An oscillating surgical saw and instrumentation system for use in shaping the end of a femur to conform it to a femoral component of an artificial knee, comprising:

an oscillating surgical saw having a body, the body having means for holding a saw blade and means for oscillating the saw blade, the body further including first and second guide pin holders disposed on opposite sides thereof and extending longitudinally therealong, each guide pin holder having a retractable guide pin therein and resilient means for urging the retractable guide pin longitudinally outward, the guide pins lying in a plane parallel to a plane in which the saw blade lies;

the instrumentation comprising at leas tone cutting block for use in making at least one cut to the femur to form a resected surface, the cutting block having a slot extending transversely and at least partially therethrough for receiving the guide pins of the saw when the saw is making the cut, means for locating and securing the cutting block on the femur wherein when the cutting block is located and secured on the femur the guide pin slot lies in a plane parallel to a plane in which the resected surface of the femur lies when it has been formed;

the guide pins cooperating with the cutting block to secure the saw against movement in all planes except the plane in which the femur is being cut.

11. The apparatus of claim 10 wherein the cutting block is used in making a plurality of cuts to the femur to form a plurality of resected surfaces, the cutting block having a plurality of guide pin slots where when the cutting block is secured on the femur one of the guide pin slots is associated with each resected surface of the femur formed by one of the cuts made using he cutting block and lies in a pane parallel to a plane in which its associated resected surface of the femur lies when it has been formed.

12. The apparatus of claim 10 wherein said at least one cutting block of the instrumentation comprises a plurality of cutting blocks including a chamfer cutting block used in making anterior and posterior chamfer cuts to the femur to form anterior and posterior resected chamfer surfaces thereon and an anterior/posterior cutting block used in making anterior and posterior cuts to the femur to form anterior and posterior resected surfaces thereon, the chamfer cutting block having first and second guide pin slots extending transversely and at least partially therethrough where when the chamfer cutting block is affixed to the femur the first guide pin slot lies in a plane parallel to a plane in which the anterior resected chamfer surface of the femur lies after it has been formed and the second guide pin slot lies in a plane parallel to a plane in which the posterior resected chamfer surface of the femur lies after it has been formed;

the anterior/posterior cutting block having first and second guide pin slots extending transversely and at lest partially therethrough where when the anterior/posterior cutting block is affixed to the femur the first guide pin slot lies in a plane parallel to a plane in which the anterior resected surface of the femur lies after it has been formed and the second guide pin slot lies in a plane parallel to a plane in which the posterior resected surface of femur lies after it has been formed;

the first and second guide pin slots of the chamfer cutting block and the first and second guide pin slots of the anterior/posterior cutting block receiving the guide pins of the oscillating surgical saw as it is used to make the anterior and posterior chamfer cuts and the anterior and posterior cuts, respectively, to secure the saw against movement in all planes except the plane in which the respective cut is being made.

13. The apparatus of claim 12 wherein the chamfer cutting block has first and second saw blade slots extending transversely therethrough associated with the first and second guide pin slots, respectively, where when the chamfer cutting block is affixed to the femur the first saw blade slot lies in the plane in which the anterior resected chamfer surface of the second saw blade slot lies in the plane in which the posterior resected chamfer surface of the femur will lie when it has been formed, the anterior/posterior cutting block having a saw blade slot extending transversely therethrough associated with the first guide pin slot where when the interior/posterior cutting block is affixed to the femur the saw blade slot lies in the plane in which the anterior resected surface of the femur will lie when it has been formed, the anterior/posterior cutting block having an edge associated with the second guide pin slot which is spaced a distance from the second guide pin slot such as to permit the saw blade of the oscillating surgical saw to pass by the edge when the guide pins of the oscillating surgical saw are received in the second guide pin slot of he anterior/posterior cutting block.

14. The apparatus of claim 12 wherein the saw body comprises an elongated body.

15. An oscillating surgical saw for use in cutting bone, comprising a body having means for holding a saw blade and means for oscillating the saw blade, the body having first and second guide pins disposed on opposite sides of the body and extending longitudinally therefrom in a plane parallel to a cutting plane in which the saw blade cuts, the guide pins being received in openings in instrumentation used to guide the saw when it is used to cut the bone to secure the saw against movement in all planes except the cutting plane.

16. The apparatus of claim 15 wherein the body of the saw includes means for retractably holding the guide pins and resilient means disposed in the holding means for urging the guide pins longitudinally outward from the holding means.

17. A cutting block for use in guiding a surgical saw when it is used for cutting bone, the cutting block including at least one planar saw blade slot extending therethrough and adapted to receive an oscillating saw blade of the surgical saw, and a single guide slot operably associated with each saw blade slot, said guide slot extending transversely and at least partially through said cutting block in a plane parallel to the plane in which said saw blade slot lies and being adapted to receive guide pins of the surgical saw to secure the saw against movement in all planes except the plane in which said saw blade slot lies.

* * * * *

UNITED STATES PATENT AND TRADEMARK OFFICE
CERTIFICATE OF CORRECTION

PATENT NO. : 5,092,869
DATED : March 3, 1992
INVENTOR(S) : Stephen H. Waldron It is certified that error appears in the above-identified patent and that said Letters Patent is hereby corrected as shown below:

Column 6, Line 47:      "block 1??" should be "block 100";

Column 7, Line 57:      "chafer" should be "chamfer";

Column 7, Line 65:      "screws 502" should be "screws 602";

Column 11, Line 59:     "t" should be "to";

Column 12, Line 4:      "inn" should be "in";

Column 14, Line 1:      "....chamfer surface of the second saw" should be "chamfer surface of the femur will lie after it has been formed and the second saw".

Signed and Sealed this

Twenty-fifth Day of May, 1993

Attest:

MICHAEL K. KIRK

Attesting Officer    Acting Commissioner of Patents and Trademarks